US006359988B1

(12) United States Patent
Espy-Wilson

(10) Patent No.: US 6,359,988 B1
(45) Date of Patent: Mar. 19, 2002

(54) PROCESS FOR INTRODUCE REALISTIC PITCH VARIATION IN ARTIFICIAL LARYNX SPEECH

(75) Inventor: Carol Espy-Wilson, Cambridge, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 09/651,530

(22) Filed: Aug. 29, 2000

Related U.S. Application Data

(60) Provisional application No. 60/152,422, filed on Sep. 3, 1999.

(51) Int. Cl.[7] .................................................. A61F 2/20

(52) U.S. Cl. .............................................. 381/70; 623/9

(58) Field of Search ................................ 381/70; 623/9

(56) References Cited

U.S. PATENT DOCUMENTS 4,338,488 A 7/1982 Lennox
5,326,349 A 7/1994 Baraff

FOREIGN PATENT DOCUMENTS

JP 07 000433 A 6/1995

OTHER PUBLICATIONS

Arslan, L.M., and Talkin, D., "Speaker Transformation Using Sentence HMM Based Alignments and Detailed Prosody Modification," *NY:IEEE, US*, 23:289–292 (1998).

Qi, Yingyong,"Replacing Tracheosophageal Voicing Sources Using LPC Synthesis," *The Journal of the Acoustical Society of America*, 88(3) :1228–1235 (1990).

Cole, David, et al., "Application of Noise Reduction Techniques for Alaryngeal Speech Enhancement", *Speech and Image Technologies for Computing and Telecommunications*, 491–493 (1997).

Parsa, V. and Jamieson, D.G., "A Comparison of High Precision F0 Extraction Algorithms for Sustained Vowels", *Journal of Speech, Language, and Hearing Research*, 42:112–126 (1999).

Shute, B., "Overcoming the Hurdle of Controlling Stoma Noise", *Advance for Speech–Language Pathologists & Audiologists*, Feb. 24, 1997.

Shute, B., "Current Trends in Electronic Larynges", *Advance for Speech–Language Pathologists & Audiologists*, Jul. 25,. 1994.

Eady, S.J., "Differences in the $F_0$ Patterns of Speech: Tone Language Versus Stress Language," *Language & Speech*, 25:29–42 (1982).

Espy–Wilson, C.Y., et al., "Enhancement of Electrolaryngeal Speech by Adaptive Filtering", *Journal of Speech, Language, and Hearing Research*, 41:1253–1264 (1998).

Oppenheim, A.V., "Speech Analysis–Synthesis Based on Homomorphic Filtering", *J. Acoust. Soc. of Amer.*, 45(2):458–465 (1969).

*Primary Examiner*—Minsun Oh Harvey
(74) *Attorney, Agent, or Firm*—Hamilton, Brook, Smith & Reynolds, P.C.

(57) ABSTRACT

In electrolaryngeal speech, an excitation signal is provided by means of a buzzer held against the neck. The buzzer is usually operated at a constant frequency. While such Transcutaneous Artificial Larynges (TALs) provide a means for verbal communication for people who are unable to use their own, the monotone F0 pattern results in poor speech quality. In the present invention, cepstral analysis is used to replace the original F0 contour of the TAL speech with a normal F0 pattern. Spectral analysis shows that this substitution results in two changes: (a) a varying F0 contour and (b) removal of steady background noise due to the leakage of acoustic energy. Perceptual tests were conducted to assess speech, before and after cepstral processing, produced by four laryngectomized speakers (2 males and 2 females). All speakers used the Servox TAL. The results indicate a clear preference for the processed speech.

4 Claims, 7 Drawing Sheets

PROCESS FOR INTRODUCE REALISTIC PITCH VARIATION IN ARTIFICIAL LARYNX SPEECH

RELATED APPLICATION

This application claims the benefit of U.S. Provisional Application No. 60/152,422, filed Sep. 3, 1999, the entire teachings of which are incorporated herein by reference.

GOVERNMENT SUPPORT

This invention was made in connection with a National Institute of Health (NIH) grant Contract Number R44-DC02925. The United States Government may have certain rights in this invention.

BACKGROUND OF THE INVENTION

A Transcutaneous Artificial Larynx (TAL) such as the Servox Inton provides a mean of verbal communication for people who have either undergone a laryngectomy or are otherwise unable to use their larynx (for example, after a tracheotomy). These devices are vibrating impulse sources held against the neck. Although some of these devices give users a choice of two frequency rates at which they can vibrate, most users find it cumbersome to switch between frequencies, even when a dial can be used for continuous pitch variation (as in the case of some of the Cooper Rand devices). Thus, the frequency of the excitation signal provided to the vocal tract from TAL devices is usually constant.

In contrast, natural speech has many pitch variations. The fundamental frequency (F0) may change several times in a single phone and may signal stress and syntactic information [1]. While most phones will have a simple rising or falling F0 pattern, some phones may contain a 'rise+fall+rise' contour. Thus, the inability to vary the pitch during TAL speech is a real shortcoming that contributes to the monotonous and unnatural quality of TAL speech.

Another source of degradation in TAL speech is the presence of a steady background signal ("noise") due to the leakage of acoustic energy from the TAL, its interface with the neck, and the surrounding neck tissue. In [2], an adaptive filtering technique was developed to remove this background noise. Perceptual experiments showed a substantial improvement in the speech quality.

A cepstral processing method we used to overcome the problems in TAL speech addressed above.

SUMMARY OF THE INVENTION

The present invention improves the quality of speech produced by users of Transcutaneous Artificial Larynges (TAL). Two major reasons why TAL speech sounds unnatural are (1) the monotone quality due to the constant rate at which the TAL device vibrates and (2) the signal that radiates from the device and the neck tissue surrounding the placement of the device on the neck. We refer to the radiated signal as "noise."

Technical Description of Invention

The technology developed processes the TAL speech in real time using several stages. First, landmarks associated with the manner in which speech is produced are detected. These landmarks divided TAL speech into the following regions: Sonorant (includes vowels, nasals and semivowels), Stops, Fricatives, True Silence and Silence (this latter category are regions where no speech signal is present; however, the TAL device is turned on so that there is still radiated noise).

Second, the sonorant regions are processed so that the constant source is replaced by a more natural source. To do this, cepstral analysis is used to deconvolve the TAL speech into (a) vocal tract information and (b) excitation information. Cepstral processing is also performed on natural speech as well. Then the excitation signal from the natural speech is convolved with the vocal tract information from TAL speech to produce the new TAL signal with varying pitch. The portion of the natural speech signal used depends on the type of pitch contour desired. If the portion of the TAL speech is at the beginning of an utterance, then we want a pitch contour that is rising. Subsequent portions of the TAL speech signal will be processed with a rising pitch contour until a stressed syllable is reached (determined by the duration of the sonorant region). Once a stressed syllable is reached, then the TAL speech is processed using natural speech that has a falling pitch contour. However, if the sonorant regions is very long, then a pitch contour that has a rise-fall-rise pattern will be used.

Third, fricative regions in the TAL speech are processed with an excitation signal extracted from a fricative region in natural speech. Similarly, stop regions in the TAL speech are processed with an excitation signal extracted from a stop region in natural speech. The same processing is used for silent regions.

A side benefit of using cepstral analysis to change the excitation signal of TAL speech with an excitation signal from natural speech is that the radiated noise in the TAL speech is also removed.

Advantages and Improvements Over Existing Methods, Devices or Materials

Presently, some TAL devices allow the users to change the rate at which it vibrates by pushing one of two buttons on the device. That is, the user has a choice of two frequencies. In addition, the Cooper Rand devices allow users to turn a knob on the device to change the rate at which it vibrates. However, from our experience with TAL users and from our conversations with speech pathologists, most users do not use any of the options. This is probably the case for several reasons. First, normal speakers naturally change their pitch without thinking about it. Thus, it is probably too difficult for speakers to stay conscious of changing their pitch. In addition, changing the rate at which these devices vibrate by using the thumb or some other finger requires too much dexterity.

As far as we know, no one has previously attempted to develop a separate device to introduce pitch variations in TAL speech.

Possible Variations and Modifications

We will continue to explore how to make the pitch changes even better. Presently, we are looking at different smoothing techniques to concatenate the different portions of the TAL speech to make sure we don't introduce any unwanted discontinuities.

Features Believed to be New (1) The use of a landmark detection program to divide the speech signal into regions.

(2) The application of cepstsral processing to this type of problem.

(3) The algorithm for generation the F0 contour (pitch variation).

Problem Solved

Improving the quality of TAL speech by (a) introducing realistic pitch variation and (b) removing the radiated background noise.

Possible Uses of Invention

The invention will be incorporated into a device that TAL users can by to improve their speech when talking over the telephone or in some other electronic mediated situation.

Disadvantages Or Limitations

Presently, the invention can be used only to improve TAL speech in electronically mediated situations.

DETAILED DESCRIPTION OF A PREFERRED EMBODIMENT

Reconvolution using Cepstral Analysis

Figure 1:
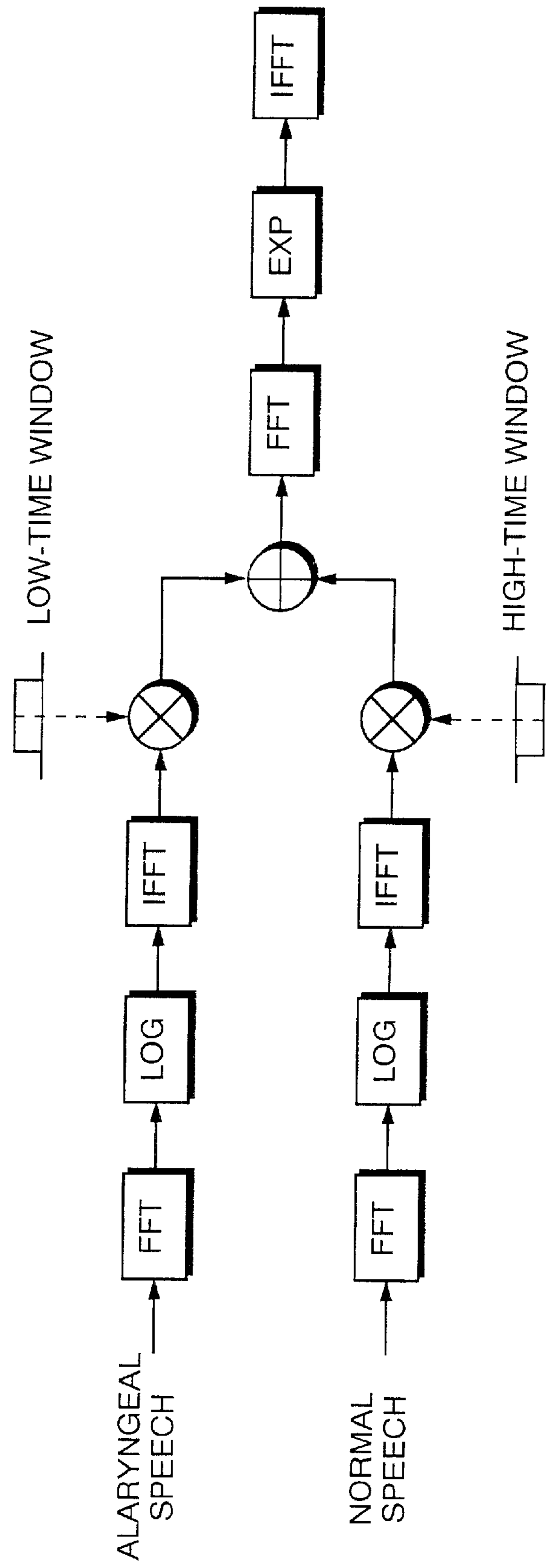
FIG. 1 is a flow chart of the reconvolution process.

The basis for the system design stems from the source-filter model of speech production [4,5]. Briefly, if we use $\otimes$ to denote the convolution operation and T for the sampling period, the digital speech signal can be represented approximately as $$s(nT)=p(nT)\otimes v(NT)$$

where p(nT) and v(nT) are respectively the excitation signal and the impulse response of the vocal tract. The spectrum of v(nT) varies slowly with frequency. However, the spectrum of p(nt) for voiced sounds varies quickly due to the harmonic structure. This difference between the source and filter characteristics results in some separation of these signals in the cepstral domain. Thus, the basic idea is to (1) separate vocal tract and excitation information in the cepstral domain for both TAL speech and normal speech and (2) combine the vocal tract information from TAL speech with the excitation information (hence a normal F0 contour) from normal speech. This process is illustrated in FIG. 1.

Although all of the speakers said the same phrase, the length of the alaryngeal utterance is usually longer than the normal utterance. Thus, before the matching process of FIG. 1, the normal utterance was usually "stretched" in some regions and compressed in others so that each phoneme in the normal utterance was of the same duration as the corresponding phoneme in the alaryngeal utterance. The stretching consisted of replicating pitch periods in regions where F0 was fairly constant. Similarly, to shorten segments, pitch periods were dropped during constant F0 regions.

The speech signal was processed with a 40 ms Hamming window and the frames occurred at 5 ms intervals. In the cepstral domain, the low-time and high-time part were obtained using a rectangular window. The highest pitch value of the normal waveforms used in this study was 230 Hz (first pitch pulse above the first 69 samples of the cepstrum) and the TAL pitch was always lower. Since the vocal tract information was always contained in the first 30 samples of the cepstrum, a cutoff of 50 samples was chosen for the rectangular window.

Subjects: Speakers

Six speakers were used a study, a normal speaker of each gender and two laryngectomee speakers of each gender. All of the subjects were native speakers of American English. For the laryngectomees, recordings were made using the Servox Inton TAL.

Subjects: Listeners

Fifteen native speakers of American English, students at Boston University, participated in the perceptual experiment. None reported any hearing loss.

Recording

All speakers were recorded in a carpeted and acoustically tiled quiet room. Each speaker read the first paragraph of the Rainbow Passage [3]. Only the phrase "they act like a prism, and form a rainbow" of the first sentence was used in the experiments reported in this paper.

Spectral Analysis

Figure 2A:
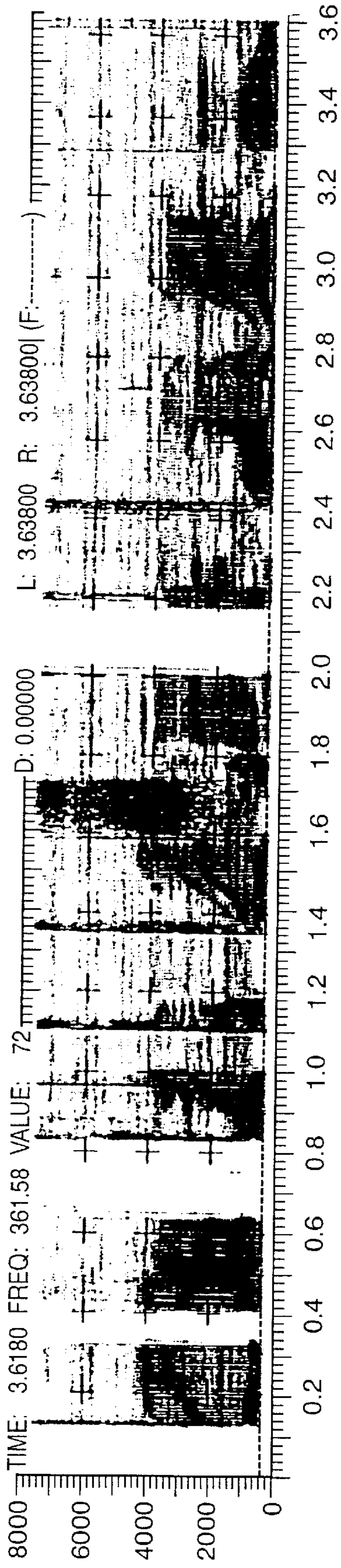
FIGS. 2A, 2B, and 2C are, respectively, a spectrogram, waveform, and F0 contour of the original TAL speech.
Figure 2B:
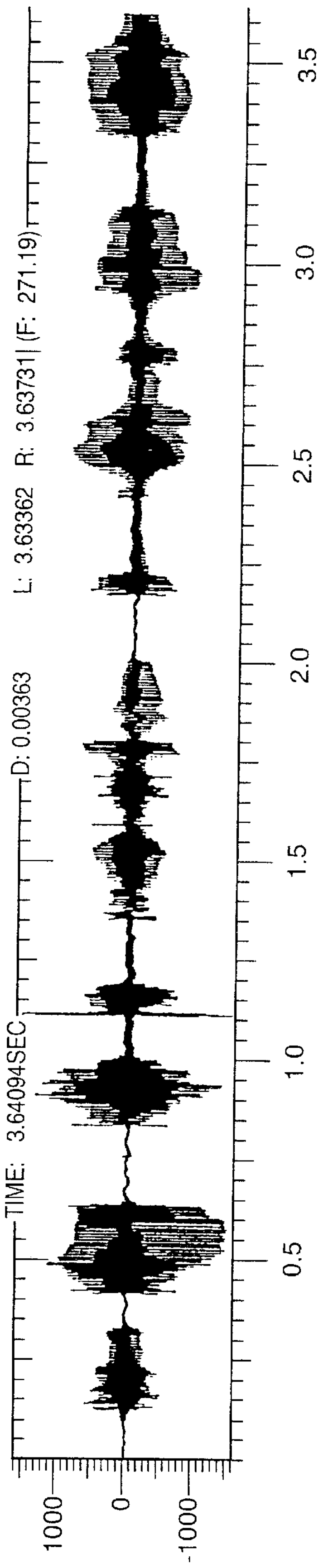
Figure 2C:
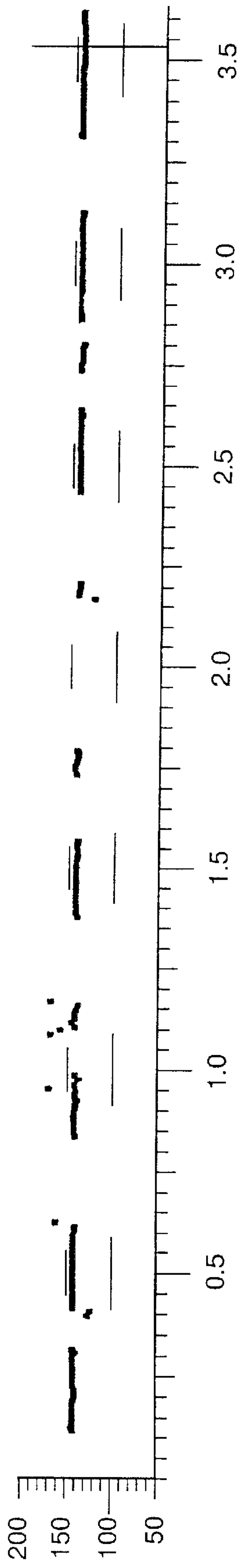
Figure 3A:
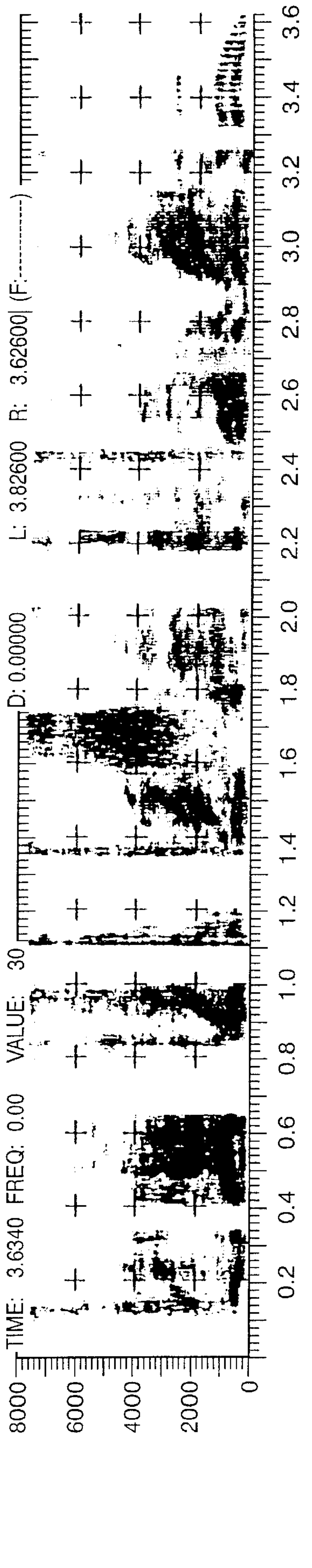
FIGS. 3A, 3B, and 3C are, respectively, a spectrogram, waveform, and F0 contour of the processed speech.
Figure 3B:
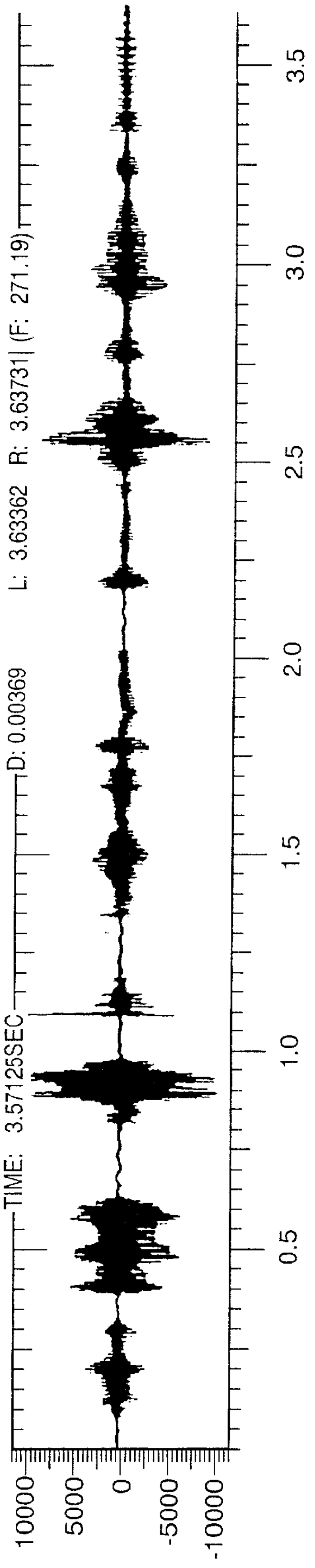
Figure 3C:
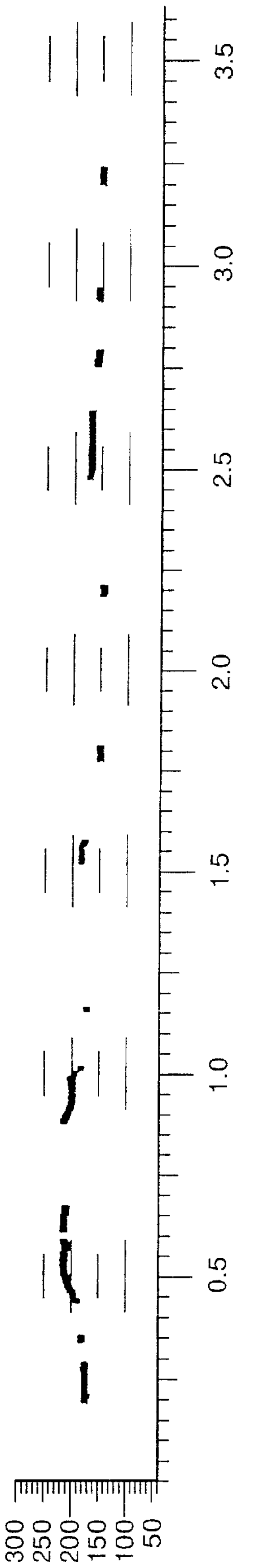

FIGS. 2A, 2B, 2C, 3A, 3B, and 3C compare the waveforms "they act like a prism and form a rainbow" spoken by one of the female laryngectomees, before and after processing. There are two main improvements. First, the pitch tracks in FIG. 3C show a varying F0 contour whereas the pitch track in FIG. 2C shows a flat F0 contour. Thus, the monotone nature of the alaryngeal speech has been removed. Note that glottalization has been introduced in the final syllable of the word "rainbow" (starting around 3.3 s) since this syllable was glottalized by the normal female speaker. (Note that the automatic pitch tracker was unable to track F0 during this syllable).

Second, the direct-radiated background noise has been removed. Although the background noise occurs throughout the original TAL speech when the device was on, it is most obvious during stop closures when no sound was coming from the mouth. For example, compare the region 1.0–1.1 s which is the stop closure of the /k/ burst in the word "like". In the original TAL speech (FIG. 2B), this interval, which should be silent, contains acoustic energy due to the radiated noise. However, in the processed TAL speech (FIG. 3B), the closure region is quiet. This removal of the background noise suggests that the noise occurs during the high-time part of the cepstum. Since the background noise contributes to the "buzzy" quality of the TAL speech [2], its removal should result in more pleasant sounding speech.

Finally, note that the formants are not as sharp in the processed speech. This fuzziness in the formants may result from the phase information. Phase was not unwrapped, since it is generally believed that Fourier Transform phase is less important in speech synthesis than magnitude.

Perceptual Analysis

A paired comparison procedure was used to perform the quality evaluation. Each pair consisted of the original TAL utterance and the processed version. Each pair was repeated four times, twice in each order. The stimulus pairs were randomized with respect to order and speaker, resulting in a set of 16 pairs. The test was administered to 15 listeners, using a computer program that first played the two utterances in a pair and then prompted the listener for a response.

The listeners were instructed to rank quality on a discrete scale of "1" to "5" based on which phrase in the pair was more pleasant. They were instructed to enter a "1" ("5") if they found the first (second) utterance to be strongly preferable to the second (first) utterance. A "2" ("4") was entered if the preference for the first (second) phrase was not strong. A "3" indicated either that there was no preference or that the difference was not perceptible. Listeners were allowed to play the pair as many times as they wished. The inter-phrase interval in each pair was one second. Fifteen practice pairs were presented to the listeners at the beginning of the test to familiarize them with the procedure, and the results for those pairs were discarded.

Table 1 lists percentage preference scores for the individual speakers as well as the mean scores.

TABLE 1 percentage preference scores for quality.

| Speaker | Strongly Prefer original | Prefer Original | No Prefer-ence | Prefer matching | Strongly Prefer Matching |
|---|---|---|---|---|---|
| female 1 | 13 | 10 | 5 | 36.7 | 35 |
| female 2 | 11.7 | 21.7 | 1.7 | 45 | 20 |
| male 1 | 15 | 18.3 | 3.3 | 41.7 | 21.7 |
| male 2 | 5 | 13.3 | 21.7 | 40 | 20 |
| average | 11.2 | 15.8 | 7.9 | 40.9 | 24.2 |

The percentage of responses pooled from all listeners and speakers that indicate a preference for the processed speech is 65% (24% indicating a strong preference). Almost 8% of the responses indicated no preference for either stimulus in the pair. The fraction of responses that showed a preference for the original phrase was 27% (11% indicating a strong preference).

CONCLUSIONS

The results show that F0 variation and removal of background noise produce a significant improvement in the quality of TAL speech. Although the laryngectomized speakers are introducing some prosodic information by varying duration and (sometimes) amplitude, F0 variation clearly improves naturalness. Thus, a procedure should be adapted to automatically generate an F0 pattern for TAL speech.

In previous work [2], significant improvement in TAL speech was made by adaptively filtering the background noise. Thus, in future applications, to test how well F0 variation alone improves the quality, one could compare the improvements made with the technique discussed in this paper with that discussed in [2]. In addition, one could investigate if unwrapping the phase will remove the fuzziness in the formants and, therefore, improve the quality of the synthesized TAL speech.

REFERENCES

1. S. Eady (1982), "Differences in the F0 patterns of speech: Tone language versus stress language," *Lang. & Speech*, 25, 29–42.
2. C. Y. Espy-Wilson, V. Chari, J. MacAuslan, C. Huang, and M. Walsh (1998), Enhancement of Electrolaryngeal Speech by Adaptive Filtering. *Journal of Speech, Language, and Hearing Research* 41, 1253–64.
3. G. Fant (1960), *Acoustic Theory of Speech Production*, the Hague, Netherlands: Mouto & Co.
4. G. Fairbanks (1960), *Voice and Articulation Drillbook*. New York: Harper and Row.
5. A. V. Oppenheim (1969), Speech Analysis-Synthesis Based on Homomorphic Filtering. *J. Acoust. Soc. of Amer.* 45, 458–65.

What is claimed is:

1. A method for improving the intelligibility of an alaryngeal speech utterance comprising the steps of:

detecting variations in the alaryngeal speech utterance to provide an alaryngeal input speech signal;

providing a normal input speech signal corresponding to the alaryngeal speech utterance as spoken by a person with a normal voice;

performing a cepstral analysis on the alaryngeal speech signal to provide representation of an alaryngeal excitation signal and an alayngeal vocal tract impulse response signal;

performing a cepstral analysis on the normal speech signal to provide representations of normal excitation signal and a normal vocal tract impulse response signal; and combining the alaryngeal vocal tract signal with the normal excitation signal to provide an output signal having improved intelligibility.

2. A method as in claim 1 additionally comprising the steps of:

dividing the alaryngeal input signal into landmark regions selected from the group consisting of sonorant regions and non-sonorant regions; and processing the sonorant region as the alaryngeal signal.

3. A method as in claim 1 wherein the step of detecting variations in the alaryngeal speech utterance additionally comprises the step of sampling the alaryngeal utterance from an alaryngeal person.

4. A method as in claim 1 wherein the normal input speech signal is read from a stored library of normal speech utterances.

* * * * *